United States Patent [19]

Toulc'Hoat et al.

[11] 3,973,432
[45] Aug. 10, 1976

[54] LACQUER HARDNESS TESTING APPARATUS

[75] Inventors: Alain Toulc'hoat; Michel Papot, both of Boulogne-Billancourt, France

[73] Assignees: Regie Nationale des Usines Renault, Boulogne-Billancourt; Automobiles Peugeot, Paris, both of France

[22] Filed: May 21, 1975

[21] Appl. No.: 579,585

[30] Foreign Application Priority Data
May 21, 1974 France .............................. 74.17572

[52] U.S. Cl. ..................................... 73/81; 73/85; 73/150 R
[51] Int. Cl.² ........................................ G01W 3/46
[58] Field of Search ................. 73/81, 82, 85, 150 R

[56] References Cited
UNITED STATES PATENTS

| 2,279,264 | 4/1942 | Hoffman | 73/150 R X |
| 2,301,733 | 11/1942 | McGovern | 73/150 |
| 2,436,435 | 2/1948 | Kent | 73/85 |
| 2,656,716 | 10/1953 | Hoggatt | 73/81 |
| 2,804,769 | 9/1957 | Clark | 73/81 |

*Primary Examiner*—Jerry W. Myracle
*Assistant Examiner*—Frederick Shoon
*Attorney, Agent, or Firm*—Fleit & Jacobson

[57] ABSTRACT

The invention relates to a lacquer hardness testing apparatus comprising a wheel formed around its outer periphery with a sharp central edge and a weight exerting its pressure on said wheel. The apparatus comprises a horizontal shaft rotatably supporting said wheel at one forked end and having its other end operatively connected to a vertical lever through means permitting an angular movement between the two members. The vertical lever is connected in the same manner to one end of another horizontal lever carrying said weight at its opposite end, said weight thus exerting a constant force on said wheel irrespective of the position of the lacquered surface to be tested. This apparatus is intended more particularly for testing the degree of curing of lacquered surfaces of the bodies of motor vehicles.

5 Claims, 4 Drawing Figures

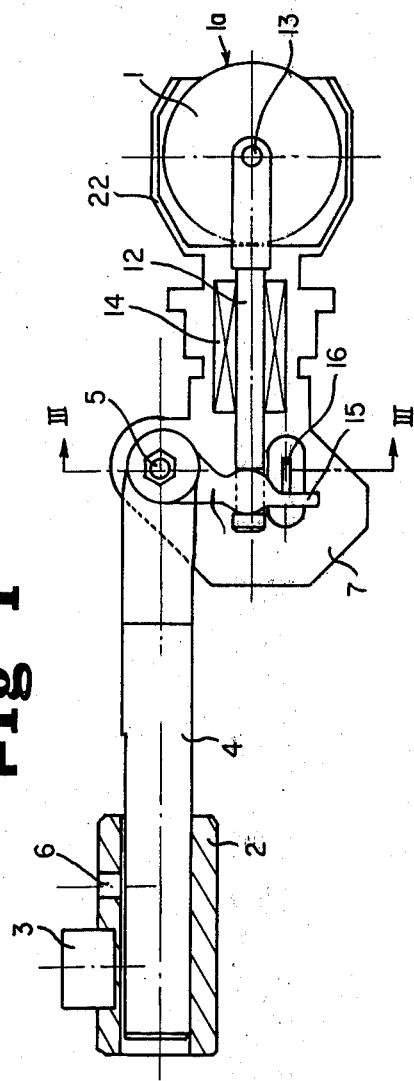
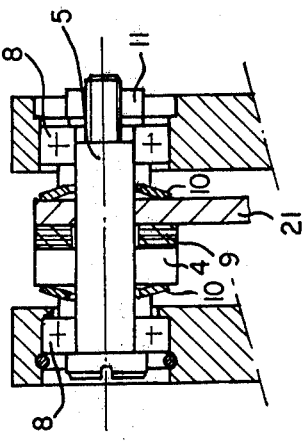
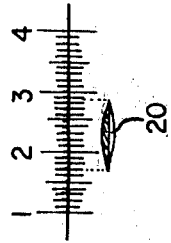

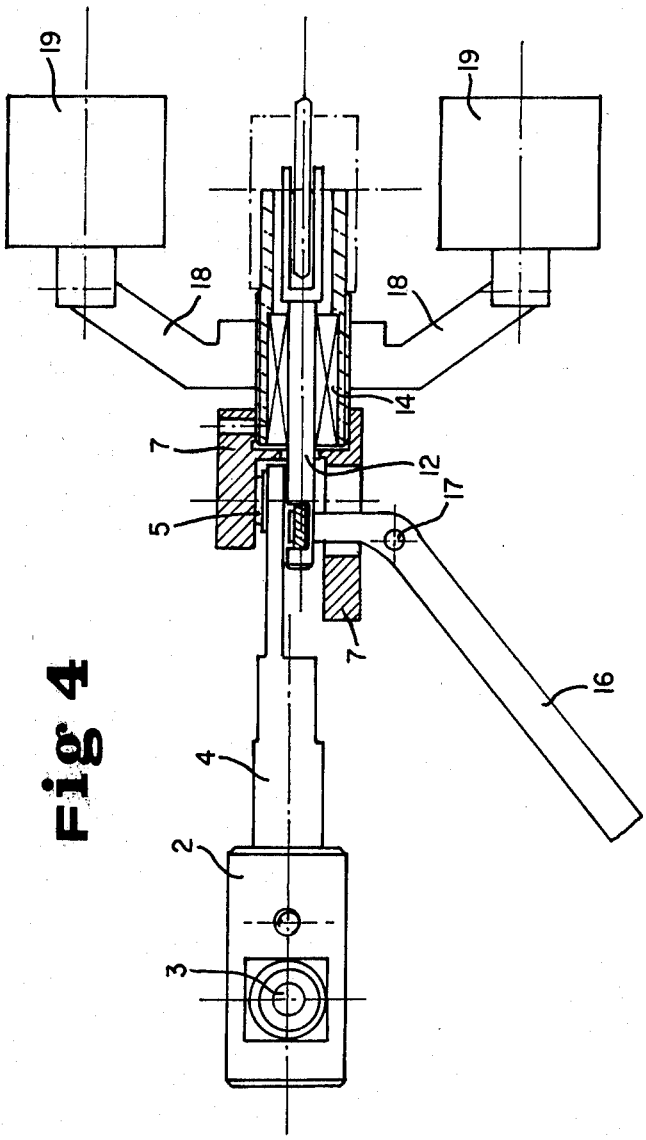

LACQUER HARDNESS TESTING APPARATUS

The present invention relates to means for checking or testing the hardness of lacquers, notably in the field of oven-cured body lacquer coatings of motor vehicles.

The advantage obtained from the possibility of measuring lacquer hardness resides in the fact that it constitutes an indirect approach of the estimation of the temperature of a lacquer curing oven for automobile bodies, in order to determine whether this temperature is sufficient or not. In fact, if the oven temperature is too low, the curing produced during a predetermined time period is inadequate and entails an inherent fragility of the cured coating. Thus, the latter may display visible marks during a subsequent handling, and in addition its adherence to the underlying metal support is not sufficient, so that blisters are most likely to develop sooner or later.

In the prior art technique of controlling the proper curing oven temperature it was customary to dispose within each vehicle a temperature recording apparatus comprising a number of probes properly distributed at suitably selected locations of the internal body surface.

Among the drawbacks characterising this method the main ones are on the one hand the relatively high cost of the recorders and probes, and on the other hand the considerable time wasted on account of the care to be exerted when fitting these probes in position. Moreover, since the data is obtained with a certain time lag, the diagrams thus obtained must be analysed by comparison with a reference curve after removing the testing apparatus from the vehicle. Finally, the parameter thus recorded is not taken from a finished product and therefore certain unknowns may interfere with the final result.

It is therefore the primary object of the present invention to avoid the above-mentioned inconveniences by providing a lacquer hardness testing apparatus capable of giving very rapidly the desired information concerning the quality of the lacquer curing on the finished product. The basic principle of this testing apparatus resides essentially in the measurement of the impression obtained on the tested lacquer by means of a small wheel pressed against the lacquer surface during a predetermined time period.

A device operating in a similar fashion is already known, which comprises a small wheel subjected to a predetermined weight and laid upon the surface to be tested. The gravity force exerted on this device causes the wheel to "sink" into the lacquer coating during a time unit by an amount depending on the softness of said coating. From the impression thus obtained the hardness properties of the coating can easily be determined.

However, this measurement method is applicable only to substantially horizontal body areas, otherwise it is obvious that the measurements are wrong or at least unreliable for, due to the inclination of the device, only the vertical component of gravity exerted on the active weight of the device is effective during the test, so that faulty measurements are obtained.

On the other hand, difficulties are also encountered for positioning the apparatus and obtaining an access to certain areas of more complicated configuration.

In contrast thereto the present invention makes it possible to operate on all surfaces to be tested, irrespective of the particular inclination thereof, and on surfaces having a relief considerably more contorted than heretofore, while allowing a substantial variation in the force exerted by the wheel so that considerably faster measurements can be made, thus combining a relatively low cost of the device with a far from negligible saving of time.

More particularly, the present invention is directed to provide a lacquer hardness testing apparatus, notably for the lacquered bodies of motor vehicles, which is capable of estimating the curing quality of the lacquers and to determine whether the temperature of the oven in which the lacquer curing operation was performed is sufficient, this apparatus comprising a wheel formed along its peripheral portion with a sharp central edge and a weight adapted to exert its pressure on said wheel, this apparatus being further characterised in that said wheel is mounted for free rotation in a fork rigidly connected to one end of a horizontal rod having its opposite end operatively connected to a vertical lever through means permitting a relative angular movement between said rod and lever, said vertical lever being connected in a similar manner to another horizontal lever of which the free end carries said weight, said other horizontal lever exerting a constant force against said wheel irrespective of the position of the tested lacquered surface.

The apparatus constituting the subject-matter of the present invention will now be described by way of illustration and non-limiting example with reference to the attached drawings, in which:

FIG. 1 is a part-sectional and side-elevational view of the testing device of this invention;

FIG. 2 illustrates a typical impression obtained by means of the testing apparatus of FIG. 1;

FIG. 3 is a vertical section taken on a larger scale along the line III—III and looking in the direction of the arrows; and FIG. 4 is a plan view from above, with parts shown in section, of the device shown in FIG. 1, the section illustrating more clearly the right-hand portion of the device at the level of the wheel carrier shaft.

Referring to the drawings, the operative portion of the device according to this invention consists essentially of a small wheel 1 provided along its outer periphery with sharp central edge 1a on which a thrust directed to the right as seen in the Figures is applied due to gravity acting upon a weight 2 and through linkage means to be described hereinafter.

More particularly, this weight 2 provided with a bubble level 3 for checking its horizontality is mounted for axial sliding movement on the end portion of a lever 4 having its opposite end fulcrumed to a horizontal transverse pivot pin 5; a means such as a screw is provided at 6 for locking the weight 2 on lever 4 in the selected longitudinal position thereon, said lever 4 comprising a longitudinal groove registering with the screw for guiding the adjustment movement of said weight 2 when the screw is slightly loosened.

As clearly shown in FIG. 3, the lever 4 is operatively connected through friction means to a lever 21 forming a variable angle about 90° with lever 4. Said friction means are enclosed in a body 7 having an apertured front portion receiving on either side rolling-contact bearings 8 supporting the pivot pin 5. The levers 4 and 21 are separated from each other by friction disks 9 and urged toward each other and against these disks 9 by spring means 10. The assembly is held in position through any suitable means, such as bolting a screwthreaded end of pivot pin 5 by means of a nut 11, the other end of this pivot pin being provided with a screw head.

In FIG. 1, the lever 21 comprises a swollen median portion engaging a matching cavity formed in one end of a rod 12 of which the opposite end is fork-shaped and carries the wheel 1 rotatably mounted on a horizontal shaft 13. This forked end and the wheel 1 are enclosed in a protection cover 22 constituting an extension of said body 7. The intermediate portion of the body 7 comprises a low-friction guide bearing 14 for rod 12.

In addition, the lever 21 has an extension beyond said swollen portion to provide a lug 15 adapted to co-act with one end of a two-armed lever 16 fulcrumed about a vertical pivot pin 17 (see FIG. 4).

Finally, it will be noted that the device is adapted to be secured to the surface area to be tested by means of a plurality of extensions 18 of body 7 of which the end portions carry magnets or suction cups 19 provided with abutment means permitting a proper positioning thereof at a constant distance.

The above-described apparatus is utilised as follows:

The device is fastened to the lacquered area to be tested by simply pressing the magnets or suction cups of the former against the latter. Then, the horizontality of weight 2 is checked by means of bubble level 3 by causing the lever 4 to slip in relation to lever 21 at the level of the friction-disk device 9, 10 centered to pivot pin 5, the position of said weight 2 being also adjusted along the lever 4 as a function of the pressure to be exerted between the edge 1a of wheel 1 and the lacquer surface. In fact, it will be seen that said position depends on the torque obtained by multiplying the weight 2 by the operative length of lever 4.

Then, with the assistance of lever 16 actuated towards the weight 2, the sharp edge 1a of wheel 1 is gently brought into light contact with the lacquered area by rotating said lever 16 about its fulcrum pin 17.

Subsequently, the testing time from the moment the weight 2 exerts its action freely upon the wheel 1 is measured. Upon completion of the testing time period the pressure exerted on the wheel 1 is relieved by actuating the lever 16 in the counter-clockwise direction about its fulcrum pin 17. Then the length of the impression 20 thus obtained (see FIG. 2) is measured, this length being proportional to its depth due to the specific configuration of the peripheral sharp edge of wheel 1, and depending likewise on the hardness of the tested lacquers and finally on the temperature of the oven in which the curing step was performed, in comparison with results obtained during previous tests with lacquers having known hardness values and oven treatment time.

It is worth pointing out that the above-mentioned operation cannot provide useful, reliable and reproducible data unless the tested lacquer coating has a sufficient thickness. In fact, if this requirement were not met the wheel 1 would contact the underlying sheet metal and the hardness estimations would obviously be wrong. This coat thickness is checked by using a magnetic apparatus of a type known per se, of which the principle of operation consists in applying a magnetized portion on the coated sheet metal body.

Then, the force necessary for removing this apparatus is measured, this force being inversely proportional to the thickness of the lacquer coating, so that useful information can be derived therefrom by comparison with a preceding gauging.

Although a specific form of embodiment of this invention has been described hereinabove and illustrated in the attached drawings, it will readily occur to those skilled in the art that various modifications and changes may be brought thereto without departing from the scope of the invention as set forth in the appended claims.

What is claimed as new is:

1. Apparatus for testing the hardness of lacquers, notably on the bodies of motor vehicles, for estimating the quality of the lacquer curing process and determining whether the temperature of the oven utilized for this process is adequate, this apparatus comprising a wheel having along its outer periphery a central sharp edge for engagement with the lacquer surface to be tested, and a weight exerting a certain pressure on said wheel, which is mounted for free rotation in a fork rigid with one end of a horizontal rod having its outer end associated with a vertical lever through means allowing an angular movement of said rod and vertical lever, said vertical lever being similarly connected to another horizontal lever supporting said weight at its free end so as to exert a constant force on said wheel for indentation of the lacquer surface with said wheel sharp edge to form an impression in the surface from which the hardness properties of the lacquer coating may be determined irrespective of the position of the tested lacquered surface.

2. Lacquer hardness testing apparatus as set forth in claim 1, wherein said horizontal and vertical levers are assembled within a body by means of a shaft extending through said body and said levers, friction disks being interposed between said levers, said levers being furthermore urged against each other by spring means.

3. Lacquer hardness testing apparatus as set forth in claim 1, wherein said weight comprises a bubble level and is longitudinally adjustable on said horizontal lever.

4. Lacquer hardness testing apparatus as set forth in claim 1, wherein said vertical lever has an extension beyond its pivotal mounting on the horizontal rod supporting said wheel, by means of a lug engaging a lever fulcrumed to a vertical pivot pin and allowing when actuated the to-and-fro movement of said wheel.

5. Lacquer hardness testing apparatus as set forth in claim 1, further comprising externally of said body extensions ending with fastening means such as magnets or suction cups for securing the apparatus to the surface coated with the lacquer to be tested.

* * * * *